United States Patent [19]

Prinzbach et al.

[11] 4,442,299

[45] Apr. 10, 1984

[54] DIEPOXYCYCLOHEXANE DERIVATIVES

[75] Inventors: Horst Prinzbach; Reinhard Schwesinger; Reinhold Keller, all of Freiburg, Fed. Rep. of Germany

[73] Assignee: BASF Aktiengesellschaft, Fed. Rep. of Germany

[21] Appl. No.: 371,014

[22] Filed: Apr. 22, 1982

Related U.S. Application Data

[63] Continuation of Ser. No. 28,738, Apr. 10, 1979, abandoned, which is a continuation of Ser. No. 891,014, Mar. 28, 1978, abandoned, which is a continuation of Ser. No. 710,458, Aug. 2, 1976, abandoned.

[30] Foreign Application Priority Data

Aug. 23, 1975 [DE] Fed. Rep. of Germany ....... 2537682

[51] Int. Cl.$^3$ .......................................... C07D 303/08
[52] U.S. Cl. ..................................... 549/545; 549/546
[58] Field of Search ........................................ 549/545

[56] References Cited

PUBLICATIONS

Chemical Abstracts, vol. 83, (1975), 193608z, 193609a.
J. Meinwald et al., Jour. Am. Chem. Soc., vol. 80, (1958), pp. 3134–3135.
Angew. Chem. Internat. Edit., vol. 11, (1972), No. 10, pp. 935–943.

*Primary Examiner*—Norma S. Milestone
*Attorney, Agent, or Firm*—Keil & Witherspoon

[57] ABSTRACT

New bromoepoxy-cyclohexenes and their derivatives, which are starting compounds for units used to synthesize natural compounds, e.g. cyclitols or aminocyclitols.

3 Claims, No Drawings

DIEPOXYCYCLOHEXANE DERIVATIVES

This is a continuation of application Ser. No. 28,738, filed Apr. 10, 1979, now abandoned, which is a continuation of Ser. No. 891,014, filed Mar. 28, 1978, now abandoned, which is a continuation of Ser. No. 710,458, filed Aug. 2, 1976, the entire disclosure of which is hereby incorporated by reference, and which is now abandoned.

The present invention relates to compounds of the formula I

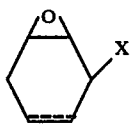

where the broken line is a double bond or an oxygen atom bonded in the form of an epoxide, and X is chlorine, bromine, or OH, which may be esterified or etherified. The invention further relates to the manufacture of the compounds and in particular to the manufacture of the pure isomers (with regard to the spatial configuration of the substituent X).

In the case of the compounds where X is OH, which can be esterified, suitable acid components are, e.g., formic acid, acetic acid, benzoic acid (where phenyl may be unsubstituted, or monosubstituted or disubstituted by chlorine or nitro) or methanesulfonic acid. Where the OH is etherified, suitable ether components are, eg. phenol, which may be unsubstituted or monosubstituted or disubstituted by $NO_2$, or benzyl alcohol.

The bromo-epoxy-cyclohexenes of the invention are obtained by brominating 4,5-epoxy-cyclohexene with N-bromo-succinimide in an anhydrous solvent. The corresponding chloro-epoxy-cyclohexenes are obtained by chlorination with tert.-butyl hypochlorite, whilst exposing the mixture to light, under conventional conditions.

In a particularly advantageous embodiment, the bromination is carried out in anhydrous carbon tetrachloride in the presence of a catalytic amount of azo-bis-isobutyronitrile, at the boil, whilst passing ethylene through the reaction mixture to prevent side-reactions.

After completion of the reaction, and after cooling, the succinimide is filtered off and the reaction solution can advantageously be purified by passing through a column filled with silica gel, after which the solvent is advantageously distilled off under reduced pressure. The residue is advantageously dissolved in methanol, using 3 parts of methanol per part by weight of epoxy-cyclohexane employed for the bromination. On leaving the mixture to stand at from −50° to −60° C., the sparingly soluble 1,4-dibromo-epoxy-cyclohexenes which have formed, in small amounts, as by-products under the above conditions, crystallize out.

An isomer mixture of endo-bromo-epoxy-cyclohexene and exo-bromo-epoxy-cyclohexene remains, in which the endo and exo compounds are present in a ratio of about 1:9. The two isomer mixtures can be separated chromatographically on silica gel, eg. using benzene or methylene chloride/carbon tetrachloride (1:4).

To prepare the dipoxides of the invention, of the formula I, in particular the cis-compounds in respect of the spatial configuration of the two epoxide rings, the isomer mixture obtained or, if appropriate, the pure endo- or exo-bromo-compound is epoxidized by conventional methods, the epoxidation advantageously being carried out with trifluoroperacetic acid in chloroform.

The mixture is worked up in the conventional way by extracting the organic solvent by shaking with water, distilling off the solvent and recrystallizing the residue.

If an isomer mixture, obtained from the bromination, in which the ratio of endo compound to exo compound is about 1:9, is used, approximately the same isomer ratio with regard to the position of the bromine atom is found in the bromo-cis-diepoxy-cyclohexane. On recrystallization from methanol, exo-bromo-cis-diepoxy-cyclohexane can be obtained pure.

Preparation of the endo-bromo-diepoxy compound, present in substantially smaller amount, in a pure form is only possible after repeated fractional crystallization from methanol.

The subject matter of the process according to the invention for the manufacture of the compounds of the formula I also embraces setting up isomerization equilibria in the mixture of the two isomeric bromides in an organic solvent in the presence of a catalytic amount of a soluble organic or inorganic bromine salt, in order to increase the proportion of a particular isomer, and the crystallization of the latter.

Particularly suitable organic solvents are chlorinated hydrocarbons, eg. methylene chloride or chloroform, ketones, eg. acetone, and nitriles of lower aliphatic carboxylic acids, eg. acetonitrile. As a rule, solutions, of from 10 to 25 percent strength by weight, of the particular isomer mixture concerned are prepared, from 0.5 to 3% by weight, based on the isomer mixture, of a soluble bromide salt are added and the mixture is left to stand at from room temperature to the boiling point of the solvent used, to set up the isomerization equilibrium.

In the case of the bromo-epoxy-cyclohexenes, room temperature is preferred, whilst in the case of the bromo-diepoxy compounds the boiling point is preferred. The setting up of the isomerization equilibrium in particular depends on the solvent used and can be followed in a simple manner by thin layer chromatography on silic gel, with benzene as the migrating agent.

After setting up the particular equilibrium, the bromide salt is as a rule removed by converting it to an aqueous solution, and the isomer mixture is subjected to fractional crystallization. Preferred bromide salts which are soluble in organic solvents are tetraalkylammonium salts with lower alkyl radicals of 1 to 5 carbon atoms, eg. tetramethylammonium bromide, tetraethylammonium bromide, tetra-n-propylammonium bromide and tetra-n-butylammonium bromide. However, it is also possible for use, for example, benzyl-trialkylammonium bromides.

We have found that the equilibrium ratio of endo- to exo-bromo-epoxy-cyclohexene in methylene chloride or chloroform is 6:4 and the ratio of endo-bromo-cis-diepoxy compound to exo-bromo-cis-diepoxy compound in acetonitrile is 9:1.

The pure endo-bromo-cis-diepoxy compound can be obtained, for example, by fractional crystallization of a hot saturated solution in methanol.

The pure isomeric bromo-epoxy-cyclohexenes and bromo-diepoxy-cyclohexanes are valuable starting compounds for the controlled manufacture of substituted sterically pure 6-membered ring compounds, especially of cyclitols, aminocyclitols or their derivatives, which are constituents of natural compounds, eg. antibiotics. The preparation of these isomeric compounds in a pure form provides, for the first time, the preconditions for reactions to form a plurality of new compounds. For example, replacement reactions of the bromine atoms, and reactions at the double bond and/or at the epoxide rings can be carried out. As is shown by the Examples, the sterically pure compounds can be manufactured in high yields.

These compounds can be used, eg., as starting compounds for antibiotic intermediates, as shown by the Examples relating to 2-desoxy-streptamine and hyosamine. Desoxystreptamine or hyosamine can be used for the chemical or microbiological synthesis of antibiotics. They can be added, eg., to the nutrient media of microorganisms which synthesize anitbiotic compounds, as is described. eg., in the book on Structures and Syntheses of Aminoglyoside Antibiotics by S. Umezawa in Advances in Carboyhydrate Chemistry and Biochemistry, 30 (1974), 111 et seq., Academic Press, or as described by W. Thomas Shier et al. in Proceedings of the National Academy of Science 63 (1969), 198–204.

2-Desoxystreptamine is a constituent of the known antibiotics gentamycin, kanamycin, neomycin, paromomycin and sisomycin. Hyosamine is an N-methyl derivative of 2-desoxystreptamycin. Using the conditions described in the Examples, the epimer of 2-desoxystreptamine or hyosamine can be prepared from exo-bromo-epoxy-cyclohexene.

2-Desoxy-streptamine can be added, for example, to nutrient solutions of micro-organisms, such as the strain Streptomyces fradiae, the aminoglycoside antibiotics Neomycin B and C being obtained (F. C. Falkner, Ph. D. Thesis, University of Illinois, 1969). Using the strain Streptomyces rimosus forma paromomycinus, the aminoglycoside antibiotic Paromomycin can be obtained. In the same way, it is possible, by means of mutant micro-organisms, to replace the 2-desoxy-streptamine, in aminoglycoside antibiotics which contain 2-desoxy-streptamine as a structural unit, by epi-2-desoxy-streptamine or hyosamine (M. Kojima and A. Satoh, Journal of Antibiotics 26, 784 (1973)).

In the Examples which follow, the nomenclature corresponding to the IUPAC rules is used in relation to the designations exo and endo. Parts are by weight.

EXAMPLE 1

(1,2/3)-1,2-Anhydro-3-bromo-cyclohex-4-ene-1,2-diol and (1,2,3/0)-1,2-anhydro-3-bromo-cyclohex-4-ene-1,2-diol 96 g of 4,5-epoxycyclohexene and 1.2 l of absolute carbon tetrachloride are introduced into a 2 liter three-necked flask equipped with a stirrer, gas inlet tube, column and distillation attachment with contact thermometer (set to 73.5° C.) 200 ml of carbon tetrachloride are distilled off slowly in order azeotropically to remove residual water in the epoxide. 180 g of N-bromosuccinimide, which has been dried over KOH and then over phosphorus pentoxide under reduced pressure from a rotary vane pump at room temperature, are than added, followed by 1 g of azo-bis-isobutyronitrile, and a slight stress of ethylene is passed into the mixture throughout the reaction (at the rate of about 1 bubble per second). As soon as the air has been displaced from the inlet tube, the mixture is heated to just the right degree that after the reaction has started the solvent distils off slowly, drop by drop. The reaction is terminated after 3 hours. The mixture is allowed to cool to 0° C., the succinimide is filtered off and the reaction solution is purified over a column of 300 g of silica gel, with carbon tetrachloride as the eluant. The solvent is distilled off; the pale yellow, liquid residue corresponds to a yield of 85–90% and can be purified by distillation, boiling point 40° at $10^{-3}$ mm Hg.

$C_6H_7OBr$ (175.0): Calculated: C 41.17; H 4.03; Br 45.65. Exo compound: Found: C 41.18; H 4.13; Br 45.43. Endo-compound: Found: C 41.23; H 4.20; Br 45.38.

The exo-compound is a light yellow liquid having a solidification point of $-15°$ C. The endo-compound is obtained as a pale yellow liquid.

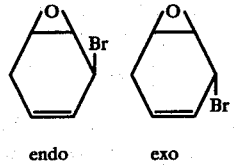

endo     exo

EXAMPLE 2

(1,2,4,5/3)-1,2:4,5-Dianhydro-3l -bromo-3-desoxy-cyclohexane-1,2,3,4,5-pentol 6.3 g (30 mmoles) of bis-trifluoroacetic anhydride are stirred with 1.2 g (30 mmoles) of 85 percent strength $H_2O_2$ for 20 minutes at 0° C., and the mixture is then taken up in 50 ml of methylene chloride and is buffered by adding an excess of dry $Na_2HPO_4$ (about 4 g), whilst cooling with ice. After 30 minutes, 4.4 g (25 mmoles) of the isomer mixture of (1,2/3)-1,2-anhydro-3-bromo-cyclohex-4-ene-1,2-diol and (1,2,3/0)-1,2-anhydro-3-bromo-cyclohex-4-ene-1,2-diol are added. According to checks by thin layer chromatography and NMR, the reaction is complete after 5 hours. The mixture is washed with 20 ml of water, the organic phase is dried over $MgSO_4$, and the solvent is stripped off on a rotary evaporator. The exo-isomer can be obtained pure by recrystallizing from methanol. Melting point 110° C. (colorless crystals).

Total yield: 4.8 g (about 85%, based on 4,5-epoxycyclohexene).

$C_6H_7O_2Br$ (191.0): Calculated: C 37.72; H 3.69; Br 41.83. Found: C 37.60; H 3.77; Br 41.68.

$^1$H-NMR (CDCl$_3$, 270 MHz): $\tau=5.21$ (m, 3-H, J=1.5 Hz): 6.59 (dd, 2(4)-H, J=4.0,=1.5 Hz); 6.80 (m, 1(5)-H); 7.21 (sd, $6_{en}$-H, J=17.5 Hz); 7.45 (dt, $6_{ex}$-H, J=17.5, 3 Hz).

$^{13}$C-NMR (CDCl$_3$): $\delta=52.42$ (2(4)-C); 49.79 (1(5)-C); 41.19 (3-C); 22.78 (6-C).

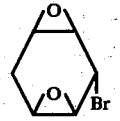

EXAMPLE 3

(1,2,3,4,5/0)-1,2:4,5-Dianhydro-3-bromo-3-desoxy-cyclohexane-1,2,3,4,5-pentol 3.0 g (17 mmoles) of (1,2,4,5/3)-1,2:4,5-dianhydro-3-bromo-3-desoxy-cyclohexane-1,2,3,4,5-pentol are dissolved in 20 ml of anhydrous acetonitrile and the solution, together with a catalytic amount (500 mg) of tetraethylammonium bromide, is refluxed for 5 hours, whereupon, according to a check by thin layer chromatography, an equilibrium mixture of the endo- and exo-isomers in the ratio of about 9:1 is formed. To remove the catalyst, the solvent is stripped off on a rotary evaporator, the solid residue is taken up in 20 ml of methylene chloride and the solution is immediately extracted by shaking with 10 ml of water. After drying the solution over MgSO$_4$ and distilling off the solvent on a rotary evaporator, crystallization of the residue from 20 ml of methanol gives 2.5 g of pure endoisomer of melting point 142° C. (colorless crystals). Yield: quantitative, if the recovered exo-isomer is included.

C$_6$H$_7$O$_2$Br (191.0): Calculated: C 37.72; H 3.69; Br 41.83. Found: C 37.90; H 3.83; Br 41.58.

$^1$H-NMR (CDCl$_3$, 270 MHz): $\tau=5.27$ (t, 3-H, H=3 Hz) 6.58 (m, 1(5)-H); 6.64 (t, 2(4)-H; J=3.4 Hz); 7.19 (dt, 6$_{en}$-H, J=17.5, 1.5 Hz); 7.72 (dt, 6$_{ex}$-H, J=17.5, 3 Hz) $^{13}$—C—NMR (CDCl$_3$): $\delta=56.40$ (2(4)-C); 53.50 (1(5)-C); 45.72 (3-C); 22.71 (6-C).

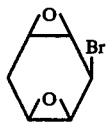

EXAMPLE 4

3-0-4-Nitrophenyl-(1,2/3)-1,2-anhydro-cyclohex-4-ene-1,2,3-triol and
3-0-4-nitrophenyl-(1,2,3/0)-1,2-anhydro-cyclohex-4-ene-1,2,3-triol 10 g (57.1 mmoles) of the mixture, obtained from the monobromination of 4,5 -epoxycyclohex-1-ene, of (1,2/3)-1,2-anhydro-3-bromo-cyclohex-4-ene-1,2-diol and (1,2,3/0)-1,2-anhydro-3-bromo-cyclohex-4-ene-1,2-diol, are taken up in 100 ml of anhydrous acetone and 16.8 g (60 mmoles) of tetramethylammonium 4-nitrophenolate are added, whilst stirring. The reaction solution is stirred for 5 hours at 20° C. The tetramethylammonium bromide formed is then filtered off, the solvent is distilled off on a rotary evaporator and the residue, obtained in a crystalline form, is taken up in 50 ml of methylene chloride. In order to free it from the residual traces of tetramethylammonium bromide, the solution is extracted by shaking with 30 ml of water. After drying the organic phase over MgSO$_4$ and distilling off the solvent on a rotary evaporator, the crystalline product is absorbed on a silica gel column (300 g of silica gel) and eluted with a 4:1 mixture of benzene and ethyl acetate. 8.7 g of pale yellow crystals of the exo-isomer, melting point 110°-112° C., and 5.8 g of pale yellow crystals of the endo-isomer, melting point 137° C., are obtained.

C$_{12}$H$_{11}$O$_4$N (233.2): Calculated: C 61.80; H 4.75; N 6.00. Exo: Found: C 61.55; H 4.79; N 6.17. Endo: Found: C 61.79; H 4.73; N 6.08.

$^1$H-NMR (CDCl$_3$, 60 MHz); exo: $\tau=1.79$ (dd, 3'(5')-H, J=8, J=2 Hz); 2.83 (dd, 2'(6')-H, =8 J=2 Hz); 4.11 (m, 4(5)-H); 4.66 (m, 3-H); 6.53 (m, 1(6)-H); 7.28 (m, 6$_{en}$(6$_{ex}$)-H).

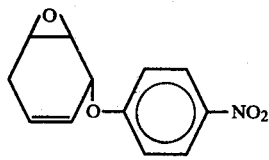

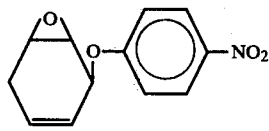

EXAMPLE 5

3-0-4-Nitrophenyl-(1,2,4,5/3)-1,2:4,5-dianhydro-cyclohexane-1,2,3,4,5-pentol 8 g (34.3 mmoles) of 3-0-4-nitrophenyl-(1,2/3)-1,2-anhydrocyclohex-4-ene-1,2,3-triol are dissolved in 20 ml of methylene chloride and 6.8 g (37 mmoles) of m-chloroperbenzoic acid are added at 0° C. After standing for 24 hours at 0° C., the solution is extracted by shaking with 20 ml of an aqueous KHCO$_3$ solution. The organic phase is dried over MgSO$_4$ and the solvent is distilled off on a rotary evaporator. The product, which is obtained in a crystalline form, can be obtained analytically pure by recrystallization from methanol. 8.7 g (98%) of colorless crystals are obtained. Melting point 183°-185° C.

C$_{12}$H$_{11}$O$_5$N (249.2): Calculated: C 57.83; H 4.44; N 5.61. Found: C 57.68; H 4.39; N 5.72.

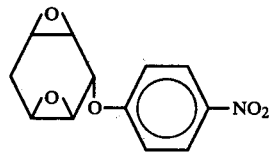

EXAMPLE 6

3-0-2,4-Dinitrophenyl-(1,2/3)-1,2-anhydro-cyclohex-4-ene-1,2,3-triol and
3-0-2,4-dinitrophenyl-(1,2,3/0)-1,2-anhydro-cyclohex-4-ene-1,2,3-triol 9 g (50 mmoles) of the mixture, obtained on monobromination of 4,5-epoxycyclohex-1-ene, of (1,2/3)-1,2-anhydro-3-bromo-cyclohex-4-ene-1,2-diol and (1,2,3/0)-1,2-anhydro-3-bromo-cyclohex-4-ene-1,2-diol, are taken up in 20 ml of chloroform, and 19.5 g (60 mmoles) of tetraethylammonium 2,4-dinitrophenolate are added. The solution is left to stand for 12 hours at 20° C. About 300 ml of chloroform are then added and the solution is extracted by shaking with four 400 ml portions of water. After drying the organic phase over MgSO$_4$ and distilling off the solvent on a rotary evaporator, the product, which is obtained in a crystalline form, is dissolved in 50 ml of a 4:1 mixture of benzene and ethyl acetate and is absorbed on, and eluted from, a column of 300 g of silica gel. 8.4 g of yellow crystals of the exo-isomer, melting point 149° C., and 5.6 g of yellow crystals of the endo-isomer, melting point 138° C., are obtained. The yield is 98%.

$C_{12}H_{10}O_6N_2$ (278.2): Calculated: C 51.80; H 3.62; N 10.06. Endo: Found: C 51.64; H 3.85; N 10.20. Exo: Found: C 51.73; H 3.68; N 10.18.

$^1$H-NMR (CDCl$_3$/D$_6$-DMSO, 60 MHz): exo: τ=1.76 (d, 3'-H, J=2 Hz); 1.93 (dd, 5'-H, J=8.5 J=2 Hz); 2.78 (d, 6'-H, J=8.5 Hz); 4.46 (m, 4(5)-H); 4.80 (m, 3-H); 6.75 (m, 1(2)-H); 7.45 (m, 6$_{ex}$(6en)-H); endo: τ=1.78 (d, 3'-H, J=2 Hz); 2.01 (dd, 5'-H, J=8.5 Hz=2 Hz); 2.71 (d, 6'-H, J=8.5 Hz); 4.63 (m, 3(4,5)-H); 6.4–6.8 (m, 1(2)-H); 7.56 (m, 6$_{ex}$(6en)-H).

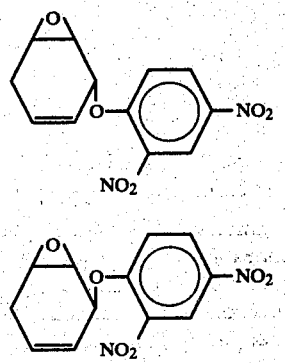

EXAMPLE 7

3-O-2,4-Dinitrophenyl-(1,2,4,5/3)-1,2:4,5-dianhydro-cyclohexane-1,2,3,4,5-pentol 5 g (18 mmoles) of 3-O-2,4-dinitrophenyl-(1,2/3)-1,2-anhydrocyclohex-4-ene-1,2,3-triol are dissolved in 20 ml of methylene chloride and 3.7 g (20 mmoles) of m-chloroperbenzoic acid are added whilst cooling with ice. After standing for 24 hours at 0° C., the solution is extracted by shaking with 20 ml of an aqueous KHCO$_3$ solution. The organic phase is dried over MgSO$_4$ and the solvent is distilled off on a rotary evaporator. The product, which is obtained in a crystalline form, can be obtained analytically pure by recrystallizing from trichloroethylene, 5.1 g (97%) od pale yellow crystals of melting point 280° C. are obtained.

$C_{12}H_{10}O_7N_2$ (294.2): Calculated: C 48.98; H 3.42; N 9.52. Found: C 48.88; H 3.37; N 9.31.

$^1$H-NMR (D$_6$-DMSO, 60 MHz): τ=1.66 (3, 3'-H, J=2 Hz); 1.90 (dd, 5'-H, J=8 Hz, J=2 Hz); 2.40 (d, 6'-H, J=8 Hz); 4.66 (m, 3-H); 6.93 (m, 1(2,4,5)-H); 7.55 (m, 6$_{ex}$(6en)-H).

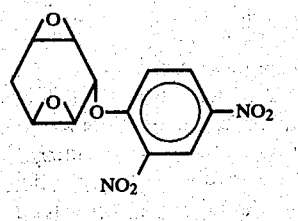

EXAMPLE 8

3-O-4-Nitrobenzoyl-(1,2,3/0)-1,2-anhydro-cyclohex-4-ene-1,2,3-triol 10 g (57.1 mmoles) of the isomer mixture of (1,2,/3)-1,2-anhydro-3-bromo-cyclohex-4-ene-1,2-diol and (1,2,3/0)-1,2-anhydro-3-bromo-cyclohex-4-ene-1,2-diol are taken up in 100 ml of anhydrous acetone and 18.5 g (60 mmoles) of tetramethylammonium-4-nitrobenzoate are added, whilst stirring. The reaction solution is stirred for 5 hours at 20° C. The tetramethylammonium bromide formed is then filtered off, the solvent is distilled off on a rotary evaporator and the residue, which is obtained in a crystalline form, is taken up in 100 ml of methylene chloride. The solution is extracted by shaking with 100 ml of water, the organic phase is dried over MgSO$_4$ and the solvent is distilled off on a rotary evaporator. The endoisomer can be obtained pure by recrystallizing from methanol.

Total yield: 14.1 g (95%).

Melting point 126° C. (pale yellow crystals).

$C_{13}H_{11}O_5N$ (261.2): Calculated: C 59.78; H 4.24; N 5.36. Found: C 59.83; H 4.37; N 5.63.

$^1$H-NMR (CDCl$_3$, 60 MHz): τ=1.70 (m, phenyl) 4.06 (m, 2-H); 4.40 (m, 3(4)-H); 6.2–6.6 (1(6)-H); 7.4 (m, 5-H).

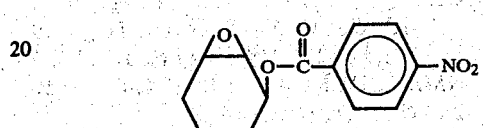

EXAMPLE 9

(1,2,3,4,5/0)-1,2:4,5-Dianhydro-3-0-methanesulfonyl-cyclohexane-1,2,3,4,5-pentol and DL-(1,2/3,4,5)-1,2:4,5-dianhydro-3-0-methanesulfonyl-cyclohexane-1,2,3,4,5-pentol The mother liquor from the N-bromosuccinimide bromination of 4,5-epoxycyclohexane is substantially freed from solvent under reduced pressure, 26.3 g (0.15 mole) of dry tetramethylammonium formate are added per mole of brominated 4,5-epoxycyclohexene, and just sufficient chloroform is then added to dissolve all the ammonium salt. After the mixture has stood for 24 hours at 20° C., it is extracted twice by shaking with water; ammonia is passed into the organic phase until the latter is saturated, and after dilution with carbon tetrachloride the organic phase is repeatedly extracted with water. The aqueous phase is concentrated to dryness under reduced pressure and the residue is distilled under reduced pressure (70° C./0.01 mm Hg). The distillate (1,2-anhydro-cyclohex-4-ene-1,2,3-triols) is dissolved in chloroform and stirred with a 20 mole % excess of m-chloroperbenzoic acid for 24 hours at 0°–10° C. The solution is substantially concentrated under reduced pressure, the residue is taken up in ether and the ether solution is extracted twice by shaking with water. The aqueous phase is concentrated to dryness under reduced pressure and the residue is thoroughly dried under the reduced pressure from a diffusion pump, and then left with 20 mole % excess of methane-sulfonic acid anhydride in pyridine for 24 hours at 0°–10° C. Excess reagent is destroyed with a little water whilst cooling with ice, the batch is poured into a mixture of ice and sulfuric acid, the whole is extracted with methylene chloride, the organic phase is again washed with water, the methylene chloride is stripped off under reduced pressure, the residue is taken up in methanol, and the solution is purified with active charcoal and left at a low temperature (about −20° C.), if necessary after seeding with the crystalline isomer. The two isomers can be separated by preparative layer chromatography (using silica gel and a 4:1 mixture of CHCl3 and acetone). The trans-compound has the higher $R_F$ value.

(1,2,3,4,5/0)-1,2:4,5-dianhydro-3-0-methanesulfonyl-cyclohexane-1,2,3,4,5-pentol Yield: 3% of colorless crystals of melting point 134°–136° C. The compound is obtained quantitatively by treatment of the compound of Example 13 with methanesulfonic acid anhydride in pyridine.

$C_7H_{10}O_5S$ (206.2): Calculated: C 40.77; H 4.89; S 15.55. Found: C 40.51; H 4.96; S 15.72.

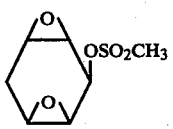

$^1$H-NMR ($D_6$-DMSO):=4.47 (mc, 3-H), 6.67 (mc, 1,2,4,5-H and $CH_3$), 7.25–8.09 (m, 6-H).

$^{13}$C-NMR ($D_6$-DMSO): ppm=75.6 (C-3), 53.8 (C-1.5), 38.9 ($CH_3$-C), 22.2 (C-6).

DL-(1,2,3/4,5)-1,2:4,5-Dianhydro-3-0-methanesulfonyl-cyclohexane-1,2,3,4,5-pentol Yield: 5% of colorless crystals of melting point 88°–89° C. The compound is obtained quantitatively by treatment of the compound of Example 14 with methanesulfonic acid anhydride in pyridine.

$C_7H_{10}O_5S$ (206.2): Calculated: C 40.77; H 4.89; S 15.55. Found: C 40.51; H 5.01; S 15.71.

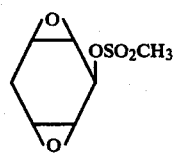

$^1$H-NMR ($DCDl_3$):=4.75 (d, 3-H), 6.50–6.93 (m, 2H), 6.78 (mc, 5H), 7.62 (mc, 6-H).

$^{13}$C-NMR ($CDCl_3$): ppm=72.3 (C-3), 51.3 (C-2), 49.6 (C-4), 49.5 (C-5), 49.1 (C-1), 39.0 ($CH_3$-C), 23.2 (C-6).

EXAMPLE 10

3-0-Acetyl-1,2,4,5/3)-1,2:4,5-dianhydro-cyclohexane-1,2,3,4,5-pentol 3.0 g (17 mmoles) of (1,2,3,4,5/0)-1,2:4,5-dianhydro-3-bromo-3-desoxycyclohexane-1,2,3,4,5-pentol are dissolved in 20 ml of anhydrous acetone and 2.7 g (20 mmoles) of anhydrous tetramethylammonium acetate are added. After heating for 2 hours under reflux, the reaction is quantitative. The tetramethylammonium bromide which has precipitated is filtered off and the solvent is distilled off on a rotary evaporator. Recrystallization of the solid residue from methanol gives 2.5 g (97%) of colorless crystals of melting point 91° C.

$C_8H_{10}O_4$ (170.1): Calculated: C 56.46; H 5.92. Found: C 56.57; H 6.17.

$^1$H-NMR ($CDCl_3$, 270 MHz); $\tau$=4.46 (m, 3-H, J=1.5 Hz); 6.86 (m, 1(5)-H); 6.93 (dd, 2(4)-H,=4,=1.4 Hz); 7.25 (sd, $6_{en}$-H, J=17.3 Hz); 7.68 (dt, $6_{ex}$-H, J=17.3, 3 Hz); 7.84 (s, $COCH_3$).

$^{13}$C-NMR ($CDCl_3$): $\delta$=169.70 (CO); 63.26 (3-C); 49.99 (2(4)-C); 49.54 (1(5)-c); 22.76 (6-C); 20.82 ($CH_3$).

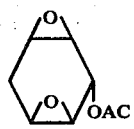

EXAMPLE 11

3-0-Acetyl-(1,2,3,4,5/0)-1,2:4,5-dianhydro-cyclohexane-1,2,3,4,5-pentol 3.0 g (17 mmoles) of (1,2,4,5/3)-1,2:4,5-dianhydro-3-bromo-3-desoxycyclohexane-1,2,3,4,5-pentol are dissolved in 20 ml of anhydrous acetone and 2.7 g (20 mmoles) of anhydrous tetramethylammonium acetate are added. After heating for 2 hours under reflux, the reaction is quantitative. The tetramethylammonium bromide which has precipitated is filtered off and the solvent is distilled off on a rotary evaporator. Recrystallization of the solid residue from methanol gives 2.5 g (97%) of colorless crystals of melting point 89° C.

$C_8H_{10}O_4$ (170.1): Calculated: C 56.46; H 5.92. Found: C 56.39; H 5.87.

$^1$H-NMR ($CDCl_3$, 270 MHz): $\tau$=4.43 (m, 3-H); 6.70 (m 1(2,4,5)-H); 7.26 (br. d, $6_{en}$-H, J=17.3 Hz); 7.80 (s, $COCH_3$); 7.84 dt. $6_{ex}$-H, J=17.3 Hz).

$^{13}$C-NMR ($CDCl_3$): $\delta$=170.84 (CO); 67.98 (3-C); 53.07 (2(4)-C); 50.73 (1(5)-C); 22.66 (6-C); 20.97 ($CH_3$).

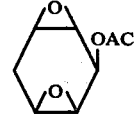

EXAMPLE 12

3.0-Formyl-(1,2,3,4,5/0)-1,2:4,5-dianhydro-cyclohexane-1,2,3,4,5-pentol 3.0 g (17 mmoles) of (1,2,4,5/3)-1,2:4,5-dianhydro-3-bromo-3-desoxycyclohexane-1,2,3,4,5-pentol are dissolved in 20 ml of anhydrous acetone and 2.4 g (20 mmoles) of tetramethylammonium formats are added. After heating for 2 hours under reflux, the reaction is quantitative. The tetramethylammonium bromide which has precipitated is filtered off and the solvent is distilled off on a rotary evaporator. Recrystallizaton of the solid residue from methanol gives 2.4 g (98%) of colorless crystals of melting point 78° C.

$C_7H_8O_4$ (156.1): Calculated: C 53.84; H 5.16. Found: C 53.81; H 4.92.

$^1$H-NMR ($CDCl_3$, 60 MHz):=1.75 (d, OOCH, J=1.5 Hz); 4.3 (m, 3-H); 6.66 (m, 1(2,4,5)-H); 7.25 (d, $6_{en}$-H, J=17.5 Hz); 7.78 (d, $6_{ex}$-H, J=17.5 Hz).

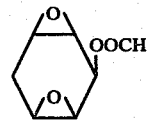

EXAMPLE 13

(1,2,3,4,5/0)-1,2:4,5-Dianhydro-cyclohexane-1,2,3,4,5-pentol 5.0 g (29.4 mmoles) of 3-0-acetyl-(1,2,3,4,5/0)-1,2:4,5-dianhydro-cyclohexane-1,2,3,4,5-penol are dissolved in 20 ml of methanol. Ammonia is passed into the solution for 10 minutes. After the mixture has stood for about 5 hours at 20° C., the hydrolysis is quantitative. After stripping off the solvent on a rotary evaporator, colorless crystals are left, which are analytically pure after recrystallization from methyl acetate. Yield: 3.5 g (94%); melting point 127° C.

$C_6H_8O_3$ (128.1): Calculated: C 56.24; H 6.29. Found: C 56.08; H 6.41.

$^1$H-NMR (CDCl$_3$, 270 MHz): $\tau=5.67$ (br.d, 3-H, J=10.5 Hz); 6.67 (m, 1(2,4,5)-H); 6.90 (d, OH, J=10.5 Hz); 7.32 (d, 6$_{en}$-H, J=17.5 Hz); 7.90 (d, 6$_{ex}$-H, J=17.5 Hz).

$^{13}$C-NMR (CDCl$_3$): $\delta=65.00$ (3-C); 54.52 (2(4)-C); 53.42 (1(5)-C); 22.01 (6-C).

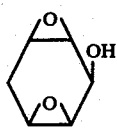

(1,2,4,5/3)-1,2:4,5-Dianhydro-cyclohexane-1,2,3,4,5-pentol 5.0 g (29.4 mmoles) of 3-0-acetyl-(1,2,4,5/3)-1,2:4,5-dianhydro-cyclohexane-1,2,3,4,5-pentol are dissolved in 20 ml of methanol. Ammonia is passed into the solution for 10 minutes. After the mixture has stood for about 5 hours at 20° C., the hydrolysis is quantitative. After stripping off the solvent on a rotary evaporator, colorless crystals are left, which are analytically pure after recrystallization from methyl acetate. Yield: 3.7 g (90%); melting point 82°-84° C.

$C_6H_8O_3$ (128.1): Calculated: C 56.24; H 6.29. Found: C 56.19; H 6.08.

$^1$H-NMR (CDCl$_3$, 60 MHz); $\tau=5.51$ (m, 3-H); 6.40 (m, OH); 6.86 (m, 1(2,4,5)-H); 7.30 (d, 6$_{en}$-H, J=17 Hz); 7.71 (d, 6$_{ex}$-H, J=17 Hz).

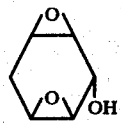

EXAMPLE 15

Pentaacetyl-2-desoxy-streptamine 3.5 g (23.4 mmoles) of (1,2,4,5/3)-1,2:4,5-dianhydro-cyclohexane-1,2,3,4,5-pentol are taken up in 10 ml of water and 1.25 g of 80% strength aqueous hydrazine monohydrate solution are added. The resulting solution is heated at 50° C. for 2 hours. After adding Raney nickel (freshly prepared from 0.5 g of alloy), hydrogenation is carried out under 10 atmospheres pressure of hydrogen for 24 hours. The catalyst is filtered off, the filtrate is purified with active charcoal and the water is distilled off as completely as possible on a rotary evaporator. The solid residue is dissolved in 20 ml of pyridine and 20 g of acetic anhydride are added. After heating the mixture for 1 hour under reflux, the pyridine and the excess acetic anhydride are distilled off on a rotary evaporator. The brown solid residue is taken up in 20 ml of water and the solution is purified with active charcoal. The water is stripped off and the solid residue is recrystallized from methanol. Yield: 7.0 g (75%). The product is identical to an authentic sample. The yield can be raised to more than 95% if the reaction with the aqueous hydrazine solution is carried out in the presence of glacial acetic acid in an amount such that only 25% of the hydrazine used is present as the free base.

$^1$H-NMR (D$_6$-DMSO, 270 MHz): $\tau=2.21$ (d, N-H, J=9 Hz); 4.93 (t, 5-H, J=10 Hz); 5.14 (t, 4(6)-H, J=10 Hz); 5.94 (dg, 1(3)-H, J=10, 4.5 Hz); 8.1 (s, OHc); 8.26 (s, NAc); 8.1–8.3 (m, CH$_2$).

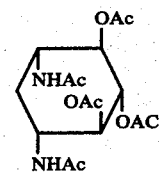

The pentaacetyl-2-desoxy-streptamine obtained is hydrolyzed to 2-desoxy-streptamine by heating for 2 hours in aqueous normal sodium hydroxide solution.

EXAMPLE 16

A reaction, carried out as described in Example 15, of (1,2,4,5/3)-1,2:4,5-dianhydro-cyclohexane-1,2,3,4,5-pentol with methylhydrazine solution, gives (±)-hyosamine in 70% yield. The yield can be raised to more than 95% by buffering with glacial acetic acid in the way described in Example 15.

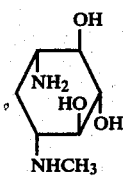

EXAMPLE 7

(1,2,3/4,6)-2,4,6-Triamino-2,4,6-tridesoxy-cyclohexane-1,2,3,4,6-pentol

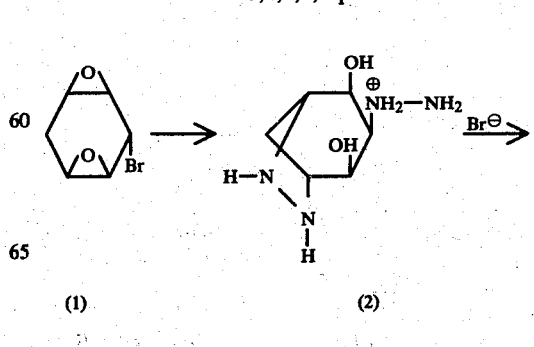

-continued

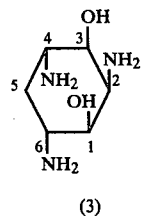

(3)

5.0 g (26.1 mmoles) of (1) are dissolved in 20 ml of methanol and 5 ml of 80% strength hydrazine monohydrate are added. The solution is heated under reflux for half an hour. The resulting solution of (2) is buffered with sodium acetate and hydrogenated, using freshly prepared Raney nickel. (3) is obtained as the crystalline pentaacetate in a yield of 70%, based on (1); melting point 313° C.

IR (KBr): 3500–3200 (N-H); 2940, 1745, 1680, 1650, 1560, 1370, 1250, 1150, 1060, 1040, 900, 740 and 580 cm$^{-1}$.

$^1$H-NMR (100 MHz, DMSO-D$_6$): $\tau$=1.95 (HN-2), 2.15 (HN-4(6)), 5.02–5.38 (1(2,3)-H), 5.55–5.88 (4(6)-H), 8.04 (OCOCH$_3$ (eq.), N-COCH$_3$(ax)), 8.16 (N-COCH$_3$(eq)), 8.72 (5a-H) 5eq.-H not recorded separately $J_{HN,2}$=8, $J_{HN, 4(6)}$=8, $J_{5a, 4(6)}$=$J_{5a, 5eq.}$=12 Hz.

$^{13}$C-NMR (DMSO-D$_6$): $\delta$=170.3 (CO-2), 169.6 (CO-4(6), 1.68.8 (CO-1(3)), 71.4 (C-1(3)), 46.9 (C-2), 44.4 (C-4(6)), 34.0 (C-5), 22.6 (N-COCH$_{3(eq.)}$-4.6), 22.3 (N-COCH$_{3ax}$-2), 20.6 (OCOCH$_{3(eq.)}$-1.3).

EXAMPLE 18

(1,2,3/4,6)-4,6-Diamino-4,6-didesoxy-cyclohexane-1,2,3,4,6-pentol (epi-desoxystreptamine)

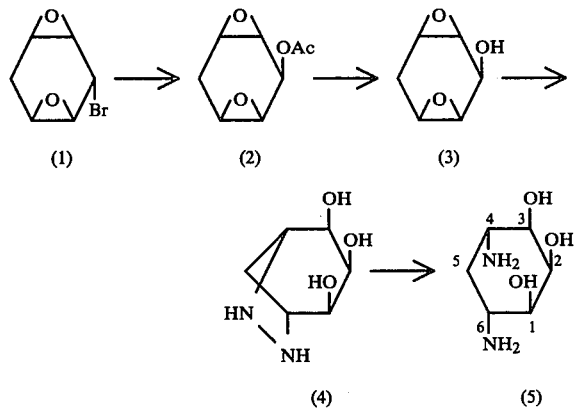

5.0 g (26.1 mmoles) of exo-monobromide (1) in 50 ml of anhydrous acetone are heated with 3.9 g (30 mmoles) of dry tetramethylammonium acetate for 5 hours under reflux. The tetramethylammonium bromide formed is filtered off, the filtrate is concentrated to dryness on a rotary evaporator, and the residue, obtained in a crystalline form, is recrystallized from methanol.

Yield: 4.3 g (97%) of (2).

(2) is quantitatively hydrolyzed to (3) in methanolic ammonia solution. The hydrazinolysis to give (4) is carried out with 3 ml of 80% strength hydrazine monohydrate in water for 2 hours at 50° C. After adding freshly prepared Raney nickel, the product is hydrogenated with hydrazine to give the epi-desoxystreptamine (5). To characterize the latter, it is acetylated with acetic anhydride in piperidine and the pentaacetate is isolated in a crystalline form. 6.5 g (70%); melting point 290° C.

IR (KBr): 3500–3150 (NH); 2960, 2940 (C-H); 1750 (—CO—O); 1660, 1640, 1560, 1370, 1240, 1220, 1080, 1040, 940 and 900 cm$^{-1}$.

$^1$N-NMR (100 MHz, DMSO-D$_6$): $\tau$=2.15 (HN-4(6)); 4.50 (2-H), 5.22 (1(3)-H), 5.92 (4(6)-H), 7.88)O-COCH-$_{3(ax)}$), 8.08 (O-COCH$_{3(eq.)}$). 8.22 (N-COCH$_{3(eq)}$), 8.70 (5a-H); $J_{NH, 4(6)}$=8; $J_{1.2}$=$J_{2.3}$=2.5, $J_{1.6}$=$J_{3.4}$=11, $J_{4(6), 5a}$=$J_{5a, 5eq.}$=12 Hz.

The location of 5eq.-H is not established; it is overlaid by acetyl-CH$_3$.

$^{13}$C-NMR (DMSO-D$_6$): $\delta$=169.9 (CO-2), 169.7 (CO-1(3)), 169.0 (CO-4(6)), 71.0 (C-1(3)), 68.2 (C-2), 44.6 (C-4(6), 33.4 (C-5, 22.6 (CH$_3$-4(6)), 20.4 (CH$_3$-1(2.3)) ppm.

EXAMPLE 19

(1,3,5/2,4)-1,3,5-Triamino-1,3,5-tridesoxy-cyclohexane-1,2,3,4,5-pentol

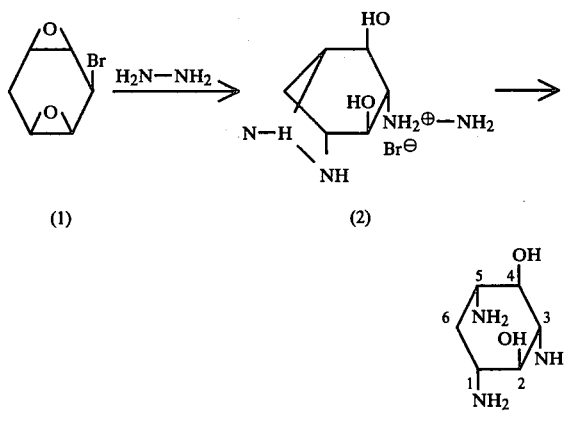

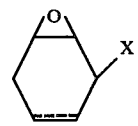

(3)

5.0 g (26.1 mmoles) of (1) are dissolved in 20 ml of methanol and 5 ml of 80% strength hydrazine monohydrate are added. The solution is heated under reflux for ½ hour. The resulting solution of (2) is buffered with sodium acetate and hydrogenated with freshly prepared Raney nickel. (3) is isolated as the pentaacetate (in a yield of 70% based on (1)), in the form of colorless crystals of melting point 280° C.

IR (KBr): 3600–3100 (N-H); 1740 (—CO—O); 1690, 1570, 1430, 1250, 1040, 930, 900 and 650 cm$^{-1}$.

$^1$H-NMR (100 MHz, DMSO-D$_6$); $\tau$=2.10 (HN-1(3.5)), $J_{HN-1(3.5)}$=8 Hz); 4.98–5.52 (2(4)-H), 5.80–6.26 (1(3.5)-H), 8.06 (OCOCH$_3$(eq.)), 8.24 (N-COCH$_3$(eq.)).

$^{13}$C-NMR (DMSO-D$_6$)+D$_2$O $\delta$=170.0 (CO-2(4)), 169.3 (CO-1(5)), 70.4 (C-2(4)), 48.8 (C-1(5), ~33 (C-6), 22.5 (N-COCH$_3$), 20.6 (O-COCH$_3$) ppm.

We claim:

1. A compound of the formula

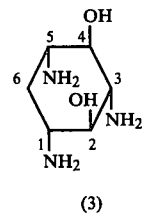

where the broken line is an oxygen atom bonded in the form of a cis epoxide, and X is endo- or exo-bromine.

2. (1,2,4,5/3)-1,2:4,5-Dianhydro-3-bromo-3-desoxy-cyclohexane-1,2,3,4,5-pentol.

3. (1,2,3,4,5/0)-1,2:4,5-Dianhydro-3-bromo-3-desoxy-cyclohexane-1,2,3,4,5-pentol.

* * * * *